US008945880B2

(12) United States Patent
Cloake et al.

(10) Patent No.: US 8,945,880 B2
(45) Date of Patent: Feb. 3, 2015

(54) THERMAL CYCLING BY POSITIONING RELATIVE TO FIXED-TEMPERATURE HEAT SOURCE

(75) Inventors: Martin Cloake, Ottawa (CA); Chris Harder, Gatineau (CA); Alan Shayanpour, Stittsville (CA); Michael Perreault, Ottawa (CA); Paul Lem, Ottawa (CA)

(73) Assignee: Spartan Bioscience, Inc., Ottawa, Ontario (CA)

( * ) Notice: Subject to any disclaimer, the term of this patent is extended or adjusted under 35 U.S.C. 154(b) by 211 days.

(21) Appl. No.: 12/462,098

(22) Filed: Jul. 29, 2009

(65) Prior Publication Data

US 2010/0075296 A1 Mar. 25, 2010

(30) Foreign Application Priority Data

Jul. 31, 2008 (CA) ..................................... 2638458

(51) Int. Cl.

*C12P 19/34* (2006.01)
*B01L 7/00* (2006.01)
*B01L 3/00* (2006.01)
*B01L 9/06* (2006.01)

(52) U.S. Cl.

CPC ................. *B01L 7/52* (2013.01); *B01L 3/5082* (2013.01); *B01L 9/06* (2013.01); *B01L 2200/142* (2013.01); *B01L 2200/147* (2013.01); *B01L 2300/042* (2013.01); *B01L 2300/0654* (2013.01); *B01L 2300/1844* (2013.01)

USPC ......................................................... 435/91.2

(58) Field of Classification Search

USPC ................................................. 435/91.2, 285

See application file for complete search history.

(56) References Cited

U.S. PATENT DOCUMENTS 4,581,333 A 4/1986 Kourilsky et al.
4,683,195 A 7/1987 Mullis et al.
4,683,202 A 7/1987 Mullis
4,800,159 A 1/1989 Mullis et al.
4,889,818 A 12/1989 Gelfand et al.
4,965,188 A 10/1990 Mullis et al.
5,023,171 A 6/1991 Ho et al.
5,038,852 A 8/1991 Johnson et al.
5,066,584 A 11/1991 Gyllensten et al.
5,075,216 A 12/1991 Innis et al.
5,079,352 A 1/1992 Gelfand et al.
5,091,310 A 2/1992 Innis
5,104,792 A 4/1992 Silver et al.
5,118,801 A 6/1992 Lizardi et al.
5,176,995 A 1/1993 Sninsky et al.
5,187,084 A 2/1993 Hallsby
5,210,015 A 5/1993 Gelfand et al.
5,283,174 A 2/1994 Arnold, Jr. et al.
5,312,728 A 5/1994 Lizardi et al.
5,386,022 A 1/1995 Sninsky et al.
5,455,175 A 10/1995 Wittwer et al.
5,525,300 A 6/1996 Danssaert et al.
5,547,842 A 8/1996 Hogan et al.
5,552,580 A 9/1996 Pfost et al.
5,589,136 A * 12/1996 Northrup et al. .............. 422/129
5,594,123 A 1/1997 Sninsky et al.
5,639,604 A 6/1997 Arnold, Jr. et al.
5,656,207 A 8/1997 Woodhead et al.
5,656,493 A 8/1997 Mullis et al.
5,658,737 A 8/1997 Nelson et al.
5,731,148 A 3/1998 Becker et al.
5,779,981 A 7/1998 Danssaert et al.
5,985,651 A 11/1999 Hunicke-Smith
6,033,880 A 3/2000 Haff et al.
6,040,166 A 3/2000 Erlich et al.
6,054,263 A * 4/2000 Danssaert et al. ................ 435/4
6,174,670 B1 1/2001 Wittwer et al.
6,197,563 B1 3/2001 Erlich et al.

(Continued)

FOREIGN PATENT DOCUMENTS

CA 2256612 12/1997
CA 2450343 1/2003

(Continued)

OTHER PUBLICATIONS

Supplementary European Search Report for EP 05734024.2, 3 pages (Mar. 15, 2010).
Braun, D., et al., "Exponential DNA Replication by Laminar Convection," Physical Review Letters, 91(15):158103-1-158103-4 (2003).
Crews, N., et al., "Continuous-flow thermal gradient PCR," Biomedical Microdevices, 10:187-195 (2007).
Dieffenback, C.W., et al., "PCR Primer: A Laboratory Manual," Cold Spring Harbor Laboratory Press (1995).
Garner, H.R., et al., "High-Throughput PCT," Biotechniques, 14:112-115 (1993).

(Continued)

*Primary Examiner* — Cynthia B Wilder
(74) *Attorney, Agent, or Firm* — Brenda Herschbach Jarrell; Charles E. Lyon; Elizabeth M. Rohlfs

(57) ABSTRACT

The thermal cycling system for performing a biological reaction at two or more different temperatures comprises: a) a heat source for setting at a fixed temperature; b) a reaction vessel containing material upon which the biological reaction is to be performed; c) mechanically-operable structure for altering the relative position of the heat source and the reaction vessel so that reaction vessel first achieves and maintains a desired first temperature in the reaction vessel for starting the carrying out of the biological reaction, and then for altering the relative position of the heat source and the reaction vessel so that the reaction vessel then achieves and maintains a second temperature for continuing the carrying out of the biological reaction on the biological material, and d) temperature-sensing structure operatively associated with the reaction vessel for controlling the altering of the relative position of the heat source and the reaction vessel so that the reaction vessel achieves and maintains the desired second temperature in the reaction vessel.

34 Claims, 4 Drawing Sheets

(56) References Cited

U.S. PATENT DOCUMENTS

| | | | | |
|---|---|---|---|---|
| 6,210,958 | B1 * | 4/2001 | Brust et al. | 435/287.2 |
| 6,514,736 | B1 | 2/2003 | Erlich et al. | |
| 6,569,627 | B2 | 5/2003 | Wittwer et al. | |
| 7,466,908 | B1 | 12/2008 | Lem et al. | |
| 2004/0115799 | A1 * | 6/2004 | Gutierrez | 435/303.1 |
| 2006/0246493 | A1 * | 11/2006 | Jensen et al. | 435/6 |
| 2008/0057544 | A1 | 3/2008 | Lem et al. | |
| 2008/0275229 | A1 | 11/2008 | Lem et al. | |

FOREIGN PATENT DOCUMENTS

| | | |
|---|---|---|
| EP | 0381501 | 8/1990 |
| EP | 0402995 | 12/1990 |
| EP | 0640828 | 3/1995 |
| EP | 0747706 | 12/1996 |
| WO | WO-9322058 | 11/1993 |
| WO | WO-98/16313 A1 | 4/1998 |
| WO | WO-03/007677 A2 | 1/2003 |
| WO | WO-03/025226 A1 | 3/2003 |
| WO | WO-2004029195 | 4/2004 |
| WO | WO-2005058501 | 6/2005 |
| WO | WO-2005100538 | 10/2005 |
| WO | WO-2005/118144 A1 | 12/2005 |

OTHER PUBLICATIONS

Gelfand, D.H., et al., "Thermostable DNA Polymerases," PCR Protocols: A Guide to Methods and Applications, San Diego, Academic Press, 129-141 (1990).

Haedicke, W., et al., "Specific and Sensitive Two-Step Polymerase Chain Reaction Assay for the Detection of Salmonella Species," Eur. J. Clin. Microbiol. Infect. Dis., 15(7):603-607 (1996).

Hendrikx, T., et al., "The Impact of the Temperature Performance of Thermal (PCR) Cyclers on the Generated Results, and the Obligation for Regular Validation of PCR Thermal Cyclers," CYCLERtest BV, Landgraaf, The Netherlands (2001).

Higuchi, R., et al., "Simultaneous Amplification and Detection of Specific DNA Sequences," Biotechnology, 10:413-417 (1992).

Higuchi, R., et al., "Kinetic PCR Analysis: Real-time Monitoring of DNA Amplification Reactions," Biotechnology, 11:1026-1030 (1993).

Higuchi, R., "Using PCR to Engineer DNA," PCR Technology: Principals and Applications for DNA Amplification, Stockton Press, 61-70 (1989).

Holland, P.M., et al., "Detection of specific polymerase chain reaction product by utilizing the 5'→3' exonuclease activity of *Thermus aquatics* DNA polymerase," Proc. Natl. Acad. USA, 88:7276-7280 (1991).

McPherson, et al., PCR: A Practical Approach, IRL Press (1991).

Morel, G., et al., "In situ reverse transcription-polymerase chain reaction. Applications for light and electron microcopy," Biology of the Cell, 90:137-154 (1998).

Morrison, L.E., et al., "Sensitive fluorescence-based thermodynamic and kinetic measurements of DNA hybridization in solution," Biochemistry, 32:3095-3104 (1993).

Nelson, D.L., et al., "Lehninger—Principles of Biology, $4^{th}$ Ed.," W. H. Freeman & Company, New York, NY, 2005, only pp. 319-321 supplied.

Neumaier, M., et al., "Fundamentals of quality assessment of molecular amplification methods in clinical diagnostics," Clinical Chemistry, 44(1):12-26 (1998).

Saiki, R..K., et al., "Enzymatic Amplification of Beta-Globin Genomic Sequences and Restriction Site Analysis for Diagnosis of Sickle Cell Anemia," Science, 230(4732):1350-1354 (1985).

Sambrook, et al., Molecular Cloning, A Laboratory Manual, $2^{nd}$ Ed. (Cold Spring Harbor Laboratory Press, Cold Spring Harbor, N.Y. (1989), Sections: 1.90-1.91; 7.37-7.57; 9.47-9.51; and 11.12-11.13, 11.45-11.47 and 11.55-11.57.

Sambrook, et al., Molecular Cloning, A Laboratory Manual, $2^{nd}$ Ed. (Cold Spring Harbor Laboratory Press, Cold Spring Harbor, N.Y. (1989) Chapter 10.

Wang, et al., "Thermal Factors Influencing Detection in Vibrio Vulnificus Using Real-time PCR," Journal of Microbiological Methods, 69:358-363 (2007).

Wittwer, C.T., et al., "Rapid Cycle DNA Amplification," The Polymerase Chain Reaction, 174-181 (1994).

Wittwer, C.T., et al., "Rapid Cycle DNA Amplification: Time and Temperature Optimization," BioTechniques, 10(1):76-83 (1991).

Wittwer, C.T., et al., "Automated polymerase chain reaction in capillary tubes with hot air," Nucleic Acids Research, 17:4353-4357 (1989).

* cited by examiner

THERMAL CYCLING BY POSITIONING RELATIVE TO FIXED-TEMPERATURE HEAT SOURCE

BACKGROUND OF THE INVENTION

1. Field of the Invention

The invention relates to the field of biological reactions which are carried out at two or more different temperatures. More particularly, it relates to chain reactions for amplifying DNA or RNA (nucleic acids), or other nucleic acid amplification reactions, e.g., Ligase Chain Reaction (LCR), or reverse transcription reactions and methods for automatically performing this process through temperature cycling. This invention also relates to thermal cyclers for automatically performing this process through temperature cycling 2. Description of the Prior Art Thermal cyclers may be used to perform Polymerase Chain Reaction (PCR), methods or other nucleic acid amplification reactions, e.g., Ligase Chain Reaction (LCR). Typically, there are three temperature-dependent stages that constitute a single cycle of PCR: template denaturation (95° C.); primer annealing (55 C 65° C.); and primer extension (72° C.). These temperatures may be cycled for 40 times to obtain amplification of the DNA target.

Some thermal cycler designs vary the temperature of a heat source to achieve denaturation, annealing, and extension temperatures. For example, U.S. Pat. No. 5,656,493 issued Aug. 12, 1997 to the Perkin-Elmer Corporation describes a heating and cooling system that raises and lowers the temperature of a heat exchanger at appropriate times in the process of nucleic acid amplification. A reaction vessel is embedded in the heat exchanger, and heat is transferred to the reaction vessel by contact with the heat exchanger. The disadvantage of such a system is that it takes time to raise and then to lower the temperature of the heat exchanger. This lengthens the time required to perform PCR.

Other designs use fixed-temperature heat blocks, and move the reaction vessel in and out of contact with the appropriate heat blocks. By saving the time required to ramp the temperature of the heat blocks, reactions may be performed in shorter times. For example, U.S. Pat. No. 5,779,981 issued Jul. 14, 1998 to Stratagene describes a thermal cycler which uses a robotic arm to move reaction vessels into contact with heat blocks set at fixed denaturation, annealing, and extension temperatures. For example, PCR may be performed with heat blocks set at fixed temperatures of 95° C., 55° C., and 72° C., respectively. The disadvantage of this system is that a separate heat block is required for each temperature setting. Each heat block takes up space and requires its own electrical control. As well, some applications may require more temperature settings than there are heat blocks. For example, the AgPath-ID™ One-Step RT-PCR Kit (Ambion) performs reverse transcription at 45° C. After reverse transcription, the reaction components may be used immediately for a 3-temperature PCR. However, if there are only three fixed-temperature heat blocks, then it will take time for one of the blocks to ramp from 45° C. to one of the three temperatures for PCR.

To minimize evaporative loss and undesirable condensation, the reagents in the reaction vessel may be overlaid with mineral oil. Alternatively, U.S. Pat. No. 5,552,580 issued Sep. 3, 1996 to Beckman Instruments Inc discloses the use of a heated lid to minimize condensation in instruments for DNA reactions.

The invention in its general form will first be described, and then its implementation in terms of specific embodiments will be detailed with reference to the drawings following hereafter. These embodiments are intended to demonstrate the principles of the invention, and the manner of its implementation. The invention in its broadest sense and more specific forms will then be further described, and defined, in each of the individual claims which conclude this Specification

SUMMARY OF THE INVENTION

Statement of Invention

A first broad aspect of the present invention provides a thermal cycling system for performing a biological reaction at two or more different temperatures: the thermal cycling system comprising: a) a heat source for setting at a fixed temperature; b) a reaction vessel containing material upon which the biological reaction is to be performed; c) mechanically-operable means for altering the relative position of the heat source and the reaction vessel so that reaction vessel first achieves and maintains a desired first temperature in the reaction vessel for starting the carrying out of the biological reaction, and then for altering the relative position of the heat source and the reaction vessel so that reaction vessel then achieves and maintains a second temperate for continuing the carrying out of the biological reaction on the biological material, and d) temperature-sensing means operatively associated with the reaction vessel for controlling the altering of the relative position of the heat source and the reaction vessel so that the reaction vessel achieves and maintains the desired second temperature in the reaction vessel.

A second broad aspect of the present invention, provides a thermal cycling system for performing a polymerase chain reaction amplification protocol comprising multiple cycles of three temperature-dependent stages of template denaturation, (e.g., about 90° C.), primer annealing (e.g., about 60° C.) and primer extension, (e.g., about 68° C.) that constitute a single cycle of PCR, the thermal cycling system comprising a) a heat source that is set at a fixed temperature; b) a reaction vessel containing material upon which a polymerase chain reaction amplification protocol is to be performed; c) mechanically-operable means for altering the relative position of the heat source and the reaction vessel so that, the temperature of the reaction vessel is achieved and is maintained for carrying out template denaturation on said material, and then for altering the relative position of the heat source and the reaction vessel so that, the temperature of the reaction vessel is achieved and is maintained for carrying out primer annealing on the material and then for altering the relative position of the heat source and the reaction vessel so that, the temperature of the reaction vessel is achieved and is maintained for carrying out primer extension on the material; and d) temperature-sensing means operatively associated with the reaction vessel for controlling the altering of the relative position of the heat source and the reaction vessel so that the reaction vessel achieves and maintains the desired second temperature in the reaction vessel.

A third broad aspect of the present invention provides a method for performing a biological reaction at two or more different temperatures, the method comprising the steps of: a) placing a reaction vessel containing a biological mixture in a position with respect to a heat source that is set at a fixed temperature to allow the reaction vessel to achieve and maintain a desired first temperature for starting the carrying out of the biological reaction, b) relatively moving the reaction vessel with respect to the heat source, thereby to achieve and maintain a second temperate for continuing the carrying out of the biological reaction on the biological material; and c) controlling the relative movement of the heat source and the reaction vessel by a temperature sensor which is operatively associated with the reaction vessel to achieve and maintain the desired reaction temperatures in the reaction vessel.

A fourth broad aspect of the present invention provides a method for performing a polymerase chain reaction amplification protocol comprising multiple cycles of three sequential temperature-dependent stages that constitute a single cycle of PCR: comprising template denaturation, primer annealing; and primer extension on a biological material, the method comprising the steps of: a) placing a reaction vessel containing the biological in a position with respect to a heat source that is set at a fixed temperature to allow the reaction vessel to achieve and maintain a desired temperature for carrying out template denaturation; b) relatively moving the reaction vessel with respect to said heat source, thereby to achieve a suitable temperature of the reaction vessel for carrying out primer annealing; d) relatively moving the reaction vessel with respect to the heat source thereby to achieve a suitable temperature of said reaction vessel for carrying out primer extension. and e) controlling the relative movement of the heat source and the reaction vessel by a temperature-sensor which is operatively associated with the reaction vessel to achieve and maintain the desired template denaturation, primer annealing; and primer extension temperatures that constitute a single cycle of PCR in the reaction vessel.

OTHER FEATURES OF THE INVENTION

By one variant of the thermal cycling system, the heat source is a block of heat retentive material including means to heat the block to, and maintain the block at, a fixed temperature.

By a variation of this variant of the thermal cycling system, the block is configured and arranged to be movable.

By another variant of the thermal cycling system, the reaction vessel is embedded in a metal sleeve, and the metal sleeve is configured and arranged to be movable.

By a variation of this variant of the thermal cycling system, the sleeve includes the temperature sensor.

By another variation of this variant of the thermal cycling system of the second aspect of the present invention, the temperature sensor, upon sensing that the temperature of the sleeve approaches the desired denaturation temperature, instructs the moving means to change the relative position of the sleeve with respect to said block to attain and maintain the desired denaturation temperature.

By another variation of this variant of the thermal cycling system of the second aspect of the present invention, the temperature sensor, upon sensing that the temperature of the sleeve approaches the desired primer annealing temperature, instructs the moving means to change the relative position of the sleeve with respect to said block to attain and maintain the desired primer annealing temperature.

By another variation of this variant of the thermal cycling system of the second aspect of the present invention, the temperature sensor, upon sensing that the temperature of the sleeve approaches the desired primer extension temperature, instructs the moving means to change the relative position of the sleeve with respect to said block to attain and maintain the desired primer extension temperature.

By another variation of this variant of the thermal cycling system, the temperature-sensor apparatus in the sleeve is operatively associated with a processor which is downloaded with an algorithm to predict the temperature being experienced by the reaction vessel, the algorithm being programmed to achieve and maintain desired temperature in the reaction vessel.

By a variation of this variant of the thermal cycling system, the temperature-sensing apparatus in the sleeve is operatively associated with the algorithm which senses that the temperature approaches the template denaturation temperature to change the relative position of the sleeve with respect to the block to attain and maintain the template denaturation temperature.

By another variation of this variant of the thermal cycling system, the temperature-sensing apparatus in the sleeve is operatively associated with the algorithm which senses that the temperature approaches the primer annealing temperature to change the relative position of the sleeve with respect to the block to attain and maintain the primer annealing temperature.

By another variation of this variant of the thermal cycling system, the temperature-sensing apparatus in the sleeve is operatively associated with the algorithm which senses that the temperature approaches the primer extension temperature to change the relative position of the sleeve with respect to the block to attain and maintain the primer extension temperature.

By another variant of the thermal cycling system, the positions of the sleeve relative to the heat source for each desired temperature is determined empirically to provide an empirical formula and the temperature sensor in the sleeve is operatively associated with this an algorithm defining empirical formula instruct the moving means change the relative position of the sleeve with respect to the block to attain and maintain the desired temperature in the reaction vessel.

By a variation of this variant of the thermal cycling system, when the temperature sensor senses that the temperature in the reaction vessel approaches the template denaturation temperature, the algorithm defining the empirical formula instructs the moving means to change the relative position of the sleeve with respect to the block to attain and maintain the template denaturation temperature.

By a variation of this variant of the thermal cycling system, when the temperature sensor senses that the temperature in the reaction vessel approaches primer annealing temperature, the algorithm defining the empirical formula instructs the moving means to change the relative position of the sleeve with respect to the block to attain and maintain primer annealing temperature by changing the relative position of the sleeve with respect to the block to attain and maintain the primer annealing temperature.

By another variation of this variant of the thermal cycling system, the temperature-sensing apparatus in the sleeve is operatively associated with the algorithm which senses that the temperature approaches the primer extension temperature to change the relative position of the sleeve with respect to the block to attain and maintain the primer extension temperature.

By another variant of the thermal cycling system, the sleeve is provided with small openings that allow the samples inside the reaction vessel to be excited and imaged as part of a fluorescence detection apparatus.

By another variant of the thermal cycling system, the reaction vessel includes a plug-style cap which is situated within the reaction vessel and the sleeve extends up the sides of the reaction vessel, so that the plug will be heated and will minimize evaporation into the top of the vessel.

By one variant of the method of aspects of the present invention, the method comprises maintaining the heat source fixed in place moving the reaction vessel.

By another variant of the method aspects of the present invention, the method comprises moving the heat source and maintaining the reaction vessel fixed in place.

By another variant of the method aspects of the present invention, the method comprises embedding the reaction vessel in a metal sleeve, and providing the metal sleeve with a temperature sensor.

By another variant of the method aspects of the present invention, the temperature sensor upon sensing that the temperature of the sleeve approaches the first desired reaction temperature, instructs moving means which are operatively associated with the sleeve, to change the relative position of the sleeve with respect to the block to attain and maintain the reaction vessel at the first desired reaction temperature.

By another variant of the method of aspects of the present invention, the temperature sensor upon sensing that the temperature of the sleeve approaches the second desired reaction temperature, instructs moving means which are operatively associated with the sleeve, to change the relative position of the sleeve with respect to the block to attain and maintain the reaction vessel at the second desired reaction temperature.

By another variant of the method of aspects of the present invention for performing a polymerase chain reaction amplification protocol, the temperature sensor, upon sensing that the temperature of the sleeve approaches the desired template denaturation temperature, instructs moving means, which are operatively associated with the sleeve, to change the relative position of the sleeve with respect to the block to attain and maintain the reaction vessel at the template denaturation temperature.

By another variant of the method of aspects of the present invention for performing a polymerase chain reaction amplification protocol, the temperature sensor, upon sensing that the temperature of the sleeve approaches the desired primer annealing temperature, instructs moving means, which are operatively associated with the sleeve, to change the relative position of the sleeve with respect to the block to attain and maintain the reaction vessel at the primer annealing temperature.

By another variant of the method of aspects of the present invention for performing a polymerase chain reaction amplification protocol, the temperature sensor upon sensing that the temperature of the sleeve approaches the desired primer extension temperature, instructs moving means, which are operatively associated with the sleeve, to change the relative position of the sleeve with respect to the block to attain and maintain said reaction vessel at the primer extension temperature.

By another variant of the method of aspects of the present invention for performing a polymerase chain reaction amplification protocol the method comprising providing a processor with an algorithm to predict the temperature being experienced by the reaction vessel, the temperature sensor cooperating with the programmed algorithm to instructs moving means, which are operatively associated with the sleeve, to change the relative position of the sleeve with respect to the block to attain and maintain temperature of the reaction vessel at the template denaturation temperature.

By another variant of the method of aspects of the present invention for performing a polymerase chain reaction amplification protocol the method comprising providing a processor with an algorithm to predict the temperature being experienced by the reaction vessel, the temperature sensor, when it senses that the temperature of the reaction vessel approaches the primer annealing temperature, cooperating with the programmed algorithm to instruct moving means, which are operatively associated with the sleeve, to change the relative position of the sleeve with respect to the block to attain and maintain temperature of the reaction vessel at the primer annealing temperature.

By another variant of the method of aspects of the present invention for performing a polymerase chain reaction amplification protocol the method comprising providing a processor with an algorithm to predict the temperature being experienced by the reaction vessel, the temperature sensor, when it senses that the temperature of the reaction vessel approaches the primer extension temperature, cooperating with the programmed algorithm to instruct moving means, which are operatively associated with the sleeve, to change the relative position of the sleeve with respect to the block to attain and maintain temperature of the reaction vessel at the primer extension temperature.

By another variant of the method of aspects of the present invention the method comprises determining empirically the positions of the sleeve relative to the heat source for each desired temperature, providing an empirical formula thereof and converting the empirical formula into an algorithm and operatively associating the temperature sensor in the sleeve this algorithm, the temperature sensor, when it senses that the temperature of the reaction vessel approaches the desired instruct the moving means change the relative position of the sleeve with respect to the block to attain and maintain the desired temperature in the reaction vessel.

By another variant of the method of aspects of the present invention for performing a polymerase chain reaction amplification protocol the method comprises determining empirically the positions of the sleeve relative to the heat source for the desired template denaturation temperature, providing an empirical formula thereof and converting the empirical formula into an algorithm and operatively associating the temperature sensor in the sleeve this algorithm, the temperature sensor, when it senses that the temperature of the reaction vessel approaches the desired template denaturation temperature instructs the moving means change the relative position of the sleeve with respect to the block to attain and maintain the desired template denaturation temperature in the reaction vessel.

By another variant of the method of aspects of the present invention for performing a polymerase chain reaction amplification protocol the method comprises determining empirically the positions of the sleeve relative to the heat source for the desired primer annealing temperature, providing an empirical formula thereof and converting the empirical formula into an algorithm and operatively associating the temperature sensor in the sleeve this algorithm, the temperature sensor, when it senses that the temperature of the reaction vessel approaches the desired primer annealing temperature instructs the moving means change the relative position of the sleeve with respect to the block to attain and maintain the desired primer annealing temperature in the reaction vessel.

By another variant of the method of aspects of the present invention for performing a polymerase chain reaction amplification protocol the method comprises determining empirically the positions of the sleeve relative to the heat source for the desired primer extension temperature, providing an empirical formula thereof and converting the empirical formula into an algorithm and operatively associating the temperature sensor in the sleeve this algorithm, the temperature sensor, when it senses that the temperature of the reaction vessel approaches the desired primer extension temperature instructs the moving means change the relative position of the sleeve with respect to the block to attain and maintain the desired primer extension temperature in the reaction vessel By another variant of the method for performing a polymerase chain reaction amplification protocol, wherein the method includes providing said sleeve with small openings that allow the samples inside the reaction vessel to be excited and imaged as part of a fluorescence detection apparatus.

By another variant of the method for performing a polymerase chain reaction amplification protocol, wherein the method includes minimizing evaporation into the top of said vessel by placing a plug-style cap reaction vessel into said reaction vessel and by positioning said sleeve to extend up the sides of the reaction vessel, so that said plug will be heated.

GENERALIZED DESCRIPTION OF THE INVENTION

In one embodiment, the invention consists of at least one heat source that is set at a fixed temperature. Contact of a reaction vessel with the heat source allows the vessel to achieve a temperature approximately the same as the heat source. A second lower temperature may be achieved and be maintained by moving the reaction vessel out of contact with the heat source, but still remaining in close proximity to the heat source. Similarly, additional lower temperatures may be achieved by positioning the reaction vessel farther away from the heat source. In this way, it is possible to achieve and to maintain multiple temperature settings using only a single heat source.

For example, the fixed-temperature heat block may be set at 95° C. The reaction vessel will equilibrate to a temperature of around 95° C. when it is brought into contact with the heated block. To achieve an annealing temperature of 55° C., the reaction vessel is moved out of contact with the heated block and is positioned at a distance where the vessel will cool down to 55° C., and be maintained at that temperature. To achieve an extension temperature of 72° C., the vessel may be moved closer to the heat block to the point where it heats up to 72° C., and is maintained at that temperature.

In a modification of the present invention, there are two fixed-temperature blocks. One block is set at a fixed temperature higher than the denaturation temperature (hot block), and the other block is set at a fixed temperature lower than the annealing temperature (cold block). The reaction vessel is embedded in a thin metal sleeve. The sleeve contains a temperature sensor. To achieve the denaturation temperature, the sleeve is contacted with the hot block. When the temperature of the sleeve approaches the desired denaturation temperature, the sleeve is backed off from the hot block, and held at a position which maintains the denaturation temperature. The temperature-sensing apparatus in the sleeve provides feedback that enables the temperature to be maintained at a constant setting by moving closer or farther away from the hot block. To achieve the annealing temperature, the sleeve is contacted with the cold block. When the temperature of the sleeve approaches the desired annealing temperature, the sleeve is backed off from the cold block, and held at a position in between the hot and cold blocks which maintains the annealing temperature. To achieve the extension temperature, the sleeve is contacted with the hot block. When the temperature of the sleeve approaches the desired extension temperature, the sleeve is backed off from the hot block, and held at a position in between the hot and cold blocks which maintains the extension temperature.

An advantage of broad aspects of the present invention is that, by using a single heat source multiple temperature conditions are enabled and, the cost and complexity of additional heat sources are saved.

Another advantage is that reducing the number of heat sources reduces the power consumption of the thermal cycler.

Another advantage is that the size of the thermal cycler may be reduced because of the space savings of fewer heat sources and associated parts.

An advantage having two blocks and of setting the hot and cold blocks at temperatures higher and lower than the desired denaturation and annealing temperatures, respectively, is that it enables the sleeve to reach more rapidly the desired denaturation and annealing temperatures, than if the blocks were set at the same temperatures as the denaturation and annealing temperatures.

There are other modifications and embodiments of the present invention. Thus, the temperature blocks may be fixed in place and the reaction vessel moves.

Alternatively, the reaction vessel may be fixed in place and the temperature blocks move.

Rather than empirically determining the reaction vessel temperature using a thermocouple embedded in the sleeve, an algorithm or formula may be used to predict the temperature being experienced by the reaction vessel when it is in close proximity with the heat source. The algorithm takes into account variables such as the starting temperature of the reaction vessel, the thermal gradient in the air adjacent to the heat source, the thermal characteristics of the sleeve, and the desired temperature to be achieved by the reaction vessel. Such an algorithm may obviate the requirement for a temperature-sensing apparatus in the sleeve.

The sleeve may have small openings that allow the samples inside the reaction vessel to be excited and imaged as part of a fluorescence detection apparatus. The reaction vessel may be directly contacted with the temperature blocks, obviating the requirement for a sleeve.

The reaction vessel may be designed to have a plug-style cap that descends into the vessel. By constructing the sleeve so it extends up the sides of the reaction vessel, the plug will be heated and minimize evaporation into the top of the vessel. This obviates the requirement for a heated lid or mineral oil overlay to prevent evaporation of the reaction vessel contents.

The foregoing summarizes the principal features of the invention and some of its optional aspects. The invention may be further understood by the description of the preferred embodiments, in conjunction with the drawings, which now follow.

BRIEF DESCRIPTION OF THE DRAWINGS

In the accompanying drawings.

DESCRIPTION OF PREFERRED EMBODIMENTS

Figure 1:
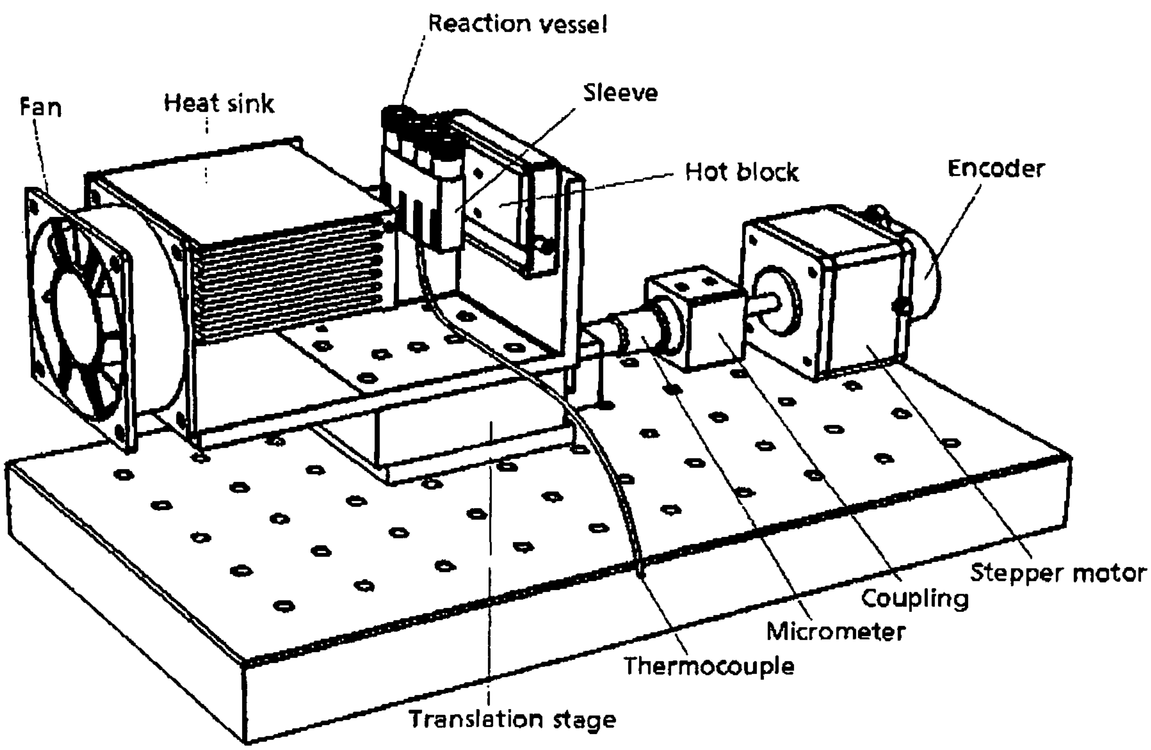
FIG. 1 is an isometric view of the setup for carrying out an embodiment of the present invention.

Description of FIG. 1

The experimental setup shown in FIG. 1 is self-explanatory and shows the heat sink, a fan, a sleeve support, the sleeve, the reaction vessels, the heated block, the translation stage, a micrometer a coupling, a stepper motor and an encoder.

Figure 2:
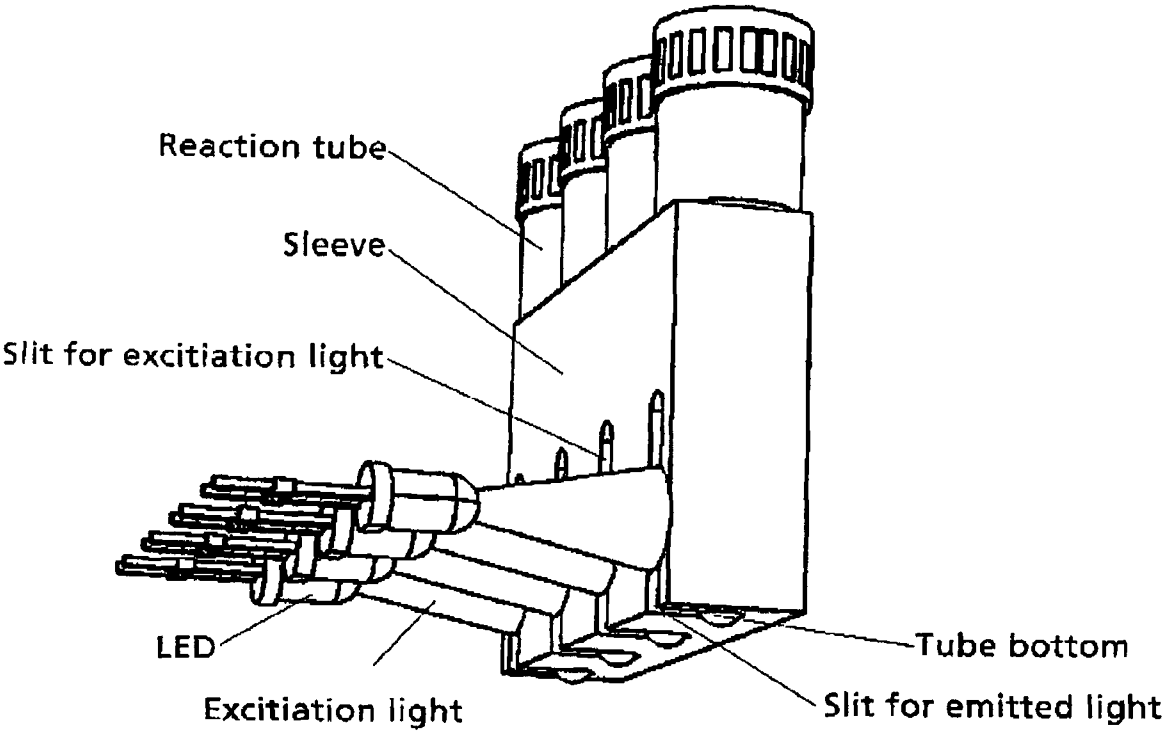
FIG. 2 is an isometric view of the sleeve of the reaction vessel modified for real time detection according to another embodiment of the present invention.

Description of FIG. 2

The sleeve modification shown in FIG. 2 is self-explanatory and shows the reaction tube, the sleeve, the LED, the excitation light the tube bottom and the slit for emitted light.

Figure 3:
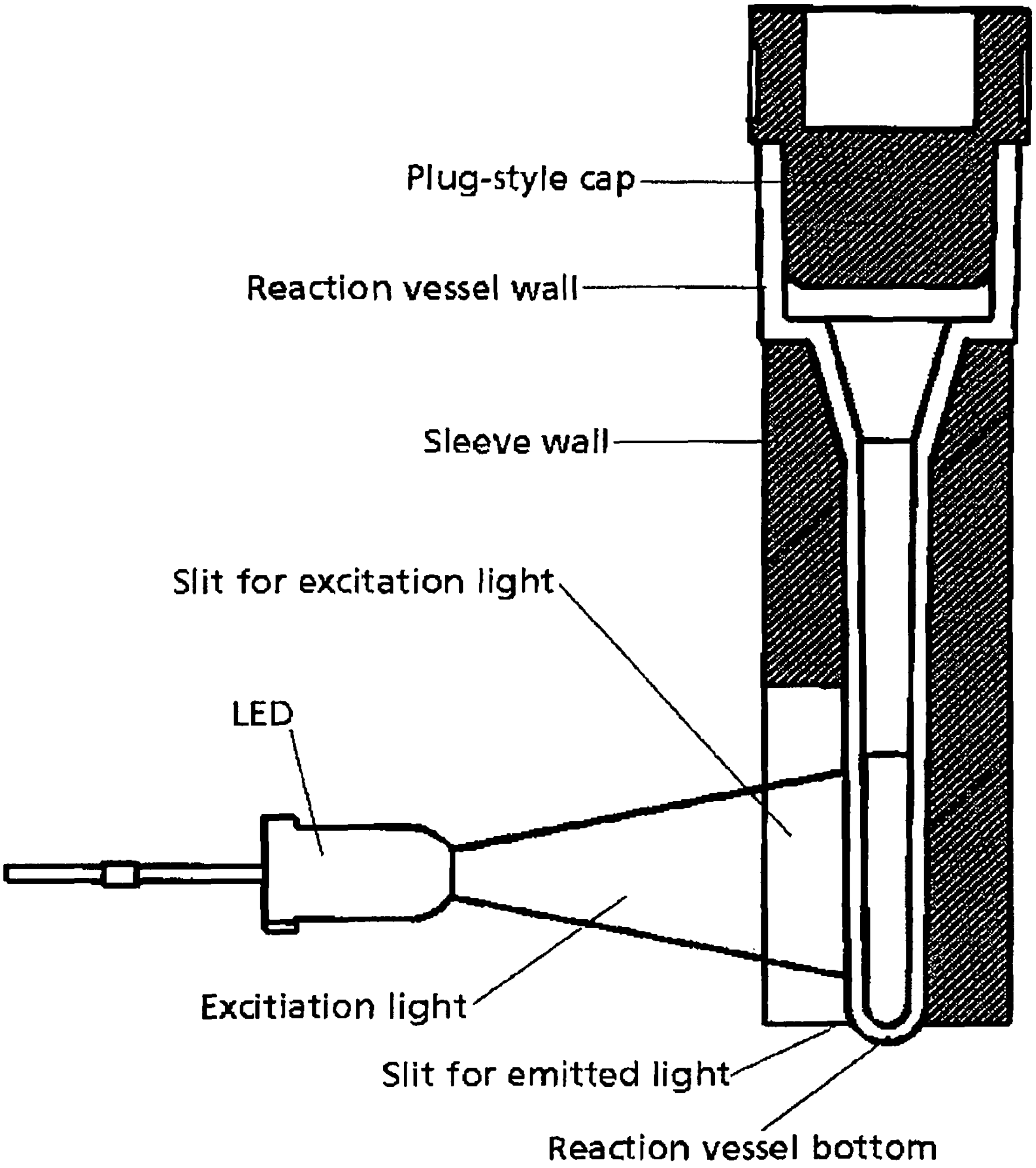
FIG. 3 is an isometric view of the sleeve of the reaction vessel modified for minimizing condensation according to another embodiment of the present invention.

Description of FIG. 3

Figure 4:
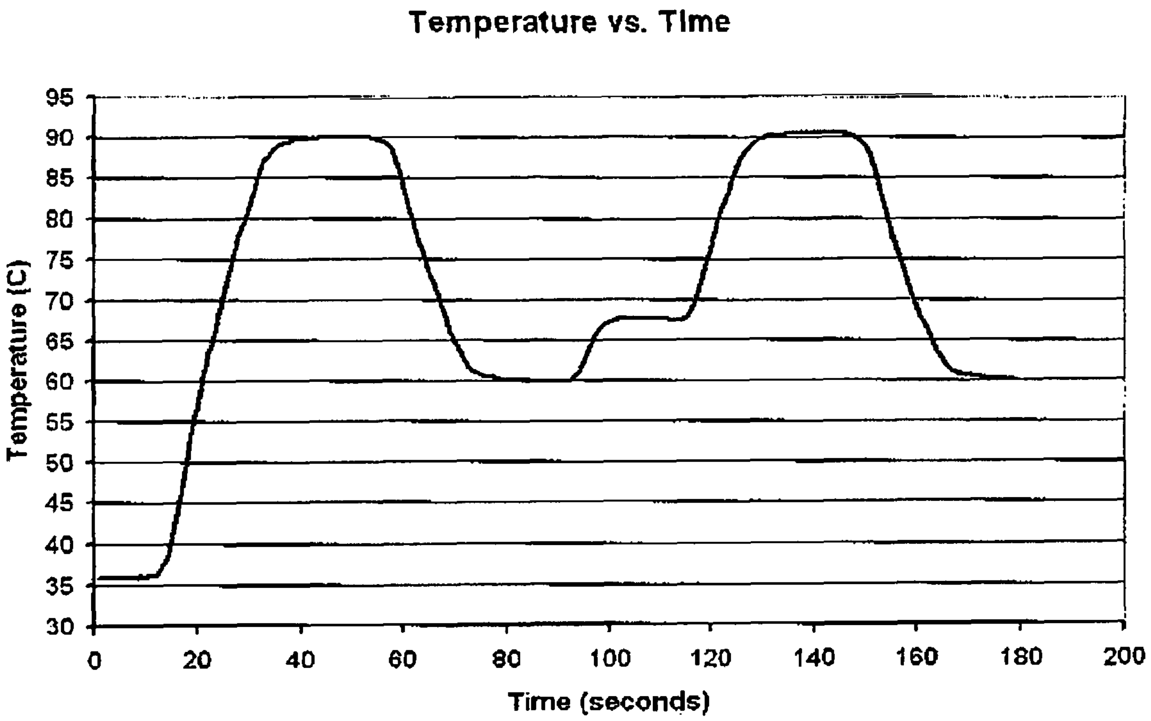
FIG. 4 shows a plot of sleeve temperature versus time when carrying out a procedure according to an embodiment of the present invention.

The sleeve modification shown in FIG. 3 is self-explanatory and shows the plug-style cap, the reaction vessel wall, the sleeve wall, the slit for excitation light, the LED, the Excitation light, the slit for emitted light and the reaction vessel bottom Description of FIG. 4

FIG. 4 shows a plot of sleeve temperature versus time for the experimental conditions.

DESCRIPTION OF PREFERRED EMBODIMENTS WITH RESPECT TO THE EXAMPLES

Example 1

To achieve, maintain, and cycle through four different temperatures using two fixed-temperature blocks.

The purpose of this example is to achieve, maintain, and cycle through four different temperatures using only one fixed-temperature heat block, and one fixed-temperature cold block. The target temperatures to achieve and maintain were 36° C., 90° C., 60° C., and 68° C. The thermal cycle transitioned from 36° C. to 90° C.; to 60° C.; to 68° C.; and to 90° C. For nucleic acid amplification, 36° C. is a suitable temperature for reverse transcription, 90° C. is suitable for denaturation, 60° C. is suitable for annealing, and 68° C. is suitable for extension.

A thermal cycling device was constructed with a fixed-temperature hot block and a fixed-temperature cold block. The hot block was constructed out of aluminum. The dimensions of the hot block were 23 mm×4:1 mm×4.3 mm. The hot block contained a 30W cartridge heater (Sun Electric, ⅛@ diameter×1@) and a thermocouple (Omega 5TC-TT-T-30-36). The cartridge heater and thermocouple were connected to a temperature controller (Omega CN 7500). The cartridge heater was also connected to a DC power supply (BK Precision 1710).

The cold block consisted of a heat sink (FANDURONT B—6 cm CPU cooler for AMD) (Duron/Tbird) that was modified to dimensions of 60 mm×60 mm×26.5 mm. A fan (Startech 12V, 60 mm×60 mm×15 mm) was mounted on the heat sink and connected to a DC power supply (BK Precision I 670A). The fan was positioned to blow across the heat sink, and through the air cavity between the hot and cold blocks. Both blocks were fixed in position. The distance between the hot and cold blocks was 22.5 mm.

An aluminum sleeve was constructed to hold four polycarbonate PCR capillary tubes (Bioron GmbH, Cat. No. A3 130100). The dimensions of the aluminum sleeve were 34 mm×19.3 mm×3.5 mm. Temperature of the sleeve was monitored via a thermocouple (Omega Type T, part #5SRTC-TT-T-30-36). The thermocouple was inserted into a 1 mm diameter hole drilled into the sleeve in the space between the middle two reaction tubes. The thermocouple was held in place with epoxy (Epotech H70E). The thermocouple was hooked up to a logging thermometer (Fluke 54 II thermometer).

The heat sink and hot block were mounted on a translation stage (Thorlabs, PT1 1@ translation stage), and the sleeve was fixed in place between them. The translation stage was movable in a linear, unidirectional horizontal motion via a micrometer. A DC motor (Anaheim Automation I 7Y00 I D-LW4-IO0SN) with encoder (Anaheim Automation E2-1000-197-1 H) was connected to the handle of the micrometer with a coupling. The DC motor and encoder were connected to a motor controller (Anaheim Automation Drive Pack DPE25601). The motor controller was connected to a computer (Dell Precision 390) which ran software to communicate with the motor controller (Anaheim Automation SMC6O WIN).

The hot block was set to 130° C. using the temperature controller. It was given 10 minutes to reach steady state. The cold block was at ambient temperature. For the sleeve, the steady state temperatures at several positions between the hot block and cold block were identified empirically using the thermocouple embedded in the sleeve. These sleeve positions are listed in the table below.

| Position (distance from hot block) | Steady State Temperature |
|---|---|
| 0.79 mm | 90° C. |
| 2.37 mm | 68° C. |
| 3.56 mm | 60° C. |
| 16.7 mm | 36° C. |

Once the system reached steady state, the motor controller software was used to position the heat sink and heat block relative to the fixed sleeve. The hot block was moved 19.1 mm from the sleeve. This placed the sleeve in contact with the cold block. The heat sink fan was turned on at the same time the motion was initiated. When the sleeve temperature reached 37.5° C., the hot block was moved 16.7 mm from the sleeve, bringing the cold block out of contact with the sleeve. When the sleeve reached 36° C., the fan was turned off. The hot block stayed at this position (16.7 mm away from the sleeve) for about 10 seconds and maintained a temperature of about 36° C. Then hot block was moved back into contact with the sleeve. When the sleeve reached 86° C., the hot block was moved to 0.79 mm away from the sleeve. The fan was turned on at the same time as the movement was initiated. When the sleeve reached 90° C., the fan was turned off the hot block stayed at this position (0.79 mm away from the sleeve) for about 10 seconds to maintain the temperature of the sleeve at about 90° C. Then the hot block was moved 19.1 mm away from the sleeve, putting the sleeve in contact with the cold block. The fan was turned on at the same time as the movement was initiated. When the sleeve reached 62.5° C., the hot block was moved to 3.56 mm away from the sleeve. When the sleeve reached 60° C., the fan was turned off. The hot block stayed at this position (3.56 mm away from the sleeve) for about 10 seconds to maintain the temperature of the sleeve at about 60° C. Then the hot block was moved into contact with the sleeve. When the sleeve reached 63.5° C., the hot block was moved to a position 2.37 mm away from the sleeve. The fan was turned on at the same time as the movement was initiated. When the sleeve reached 68° C., the fan was turned off. The hot block stayed at this position (2.37 mm away from the sleeve) for about 10 seconds and maintained a temperature of about 68° C.

The setup used in this example enabled the following temperatures to be achieved and maintained: 36° C., 90° C., 60° C., 68° C. During the maintenance portions of the thermal cycle, temperature of the sleeve was maintained at about ±0.5° C. FIG. 4 shows a plot of sleeve temperature versus time for the conditions of this example.

The setup used in this example required an operator to adjust the position of the fixed-temperature blocks manually relative to the sleeve, in response to the temperature reading from the thermocouple embedded in the sleeve. Instead of manual control, a computer algorithm may be used to adjust the position of the temperature blocks automatically to achieve and maintain the desired temperatures. This algorithm may take the form of a PID (Proportional, Integral, Derivative) control algorithm that uses sleeve temperature relative to the target temperature to define sleeve position.

Example 2

The thermal cycler described in Example 1 is made compatible with real-time detection by putting a slit in the side of the sleeve, and leaving the bottom of the sleeve open, as shown and described with reference to FIG. 2. In this way, an excitation light source is directed at the side of a tube, and the resulting emitted fluorescence is detected via a CCD camera or other detector that is imaging the bottom of sleeve. This arrangement enables the excitation source and detector to be perpendicular to each other.

Example 3

To minimize condensation, the reaction vessel includes a plug-style cap. as shown and described with reference to FIG. 3. Preferably, the plug is made of a material that conducts heat similar to the reaction vessel material. The sleeve hold is the reaction vessel such that the sides of the sleeve extend to the level of the plug or higher. In this way, the tube walls above the reaction liquid are heated, and so is the plug. This minimizes condensation of the reaction liquid on the sides of the walls or under the cap.

Conclusion

The foregoing has constituted a description of specific embodiments showing how the invention may be applied and put into use. These embodiments are only exemplary. The invention in its broadest, and more specific aspects is further described and defined in the claims which follow.

These claims, and the language used therein are to be understood in terms of the variants of the invention which have been described. They are not to be restricted to such variants, but are to be read as covering the full scope of the invention as is implicit within the invention and the disclosure that has been provided herein.

REFERENCES

Wang, 2007 (Wang 5, Levin RE. (2007). "Thermal Factors Influencing Detection of Vibrio Vulnificus Using Real-time PCR." Journal of Microbiological Methods. 69:358-363.)

The invention claimed is:

1. A thermal cycling system for performing a biological reaction at two or more different temperatures, the thermal cycling system comprising:

a) a heat source for setting at a fixed temperature;

b) a metal sleeve capable of receiving a reaction vessel containing material upon which the biological reaction is to be performed, wherein the sleeve includes a temperature-sensing means for sensing the temperature of the sleeve; and c) moving means operatively associated with the sleeve for altering the relative position of the heat source and the sleeve based on the temperature of the sleeve sensed by the temperature-sensing means, the thermal cycling system arranged and configured such that, i) in a first configuration the relative positions of the sleeve and the heat source, with respect to each other, are such that the sleeve achieves and maintains a first temperature; and ii) in a second configuration the relative positions of the sleeve and the heat source, with respect to each other, are adjusted such that the sleeve achieves and maintains a second temperature.

2. A thermal cycling system for performing a polymerase chain reaction amplification protocol comprising multiple cycles of three temperature-dependent stages of template denaturation, primer annealing and primer extension that constitute a single cycle of PCR, the thermal cycling system comprising:

a) a heat source that is set at a fixed temperature;

b) a metal sleeve capable of receiving a reaction vessel containing material upon which a polymerase chain reaction amplification protocol is to be performed, wherein the sleeve includes a temperature-sensing means for sensing the temperature of the sleeve; and c) moving means operatively associated with the sleeve for altering the relative position of the heat source and the sleeve based on the temperature of the sleeve sensed by the temperature-sensing means, the thermal cycling system arranged and configured such that, i) in a first configuration the relative positions of the sleeve and the heat source, with respect to each other, are such that the sleeve achieves and maintains a first temperature for carrying out template denaturation on the material;

ii) in a second configuration the relative positions of the sleeve and the heat source, with respect to each other, are adjusted such that the sleeve achieves and maintains a second temperature for carrying out primer annealing on the material; and iii) in a third configuration the relative positions of the sleeve and the heat source, with respect to each other, are adjusted such that the sleeve achieves and maintains a third temperature for carrying out primer extension on the material.

3. The thermal cycling system of claim 1, wherein said heat source is a block of heat retentive material including means to heat said block to, and maintain said block at a fixed temperature.

4. The thermal cycling system of claim 3, wherein said block is configured and arranged to be movable.

5. The thermal cycling system of claim 3, wherein said sleeve is configured and arranged to be movable.

6. The thermal cycling system of claim 5, wherein said temperature-sensing means is operatively associated with a processor which is downloaded with an algorithm to predict the temperature being experienced by said reaction vessel, said algorithm being based on a program to achieve and maintain a desired temperature in the reaction vessel.

7. The thermal cycling system of claim 5, wherein the positions of said sleeve relative to said heat source for achieving and maintaining the first and second temperatures were determined empirically to provide an empirical formula, and wherein said temperature-sensing means is operatively associated with a processor which is downloaded with an algorithm defining said empirical formula.

8. The thermal cycling system of claim 1, wherein said sleeve is provided with openings that are capable of allowing material inside said reaction vessel to be excited and imaged as part of a fluorescence detection apparatus.

9. The thermal cycling system of claim 1, further comprising a reaction vessel, wherein said reaction vessel includes a plug-style cap which is situated within said reaction vessel and wherein said sleeve extends up the sides of said reaction vessel, so that said plug will be heated and will minimize evaporation into the top of the reaction vessel.

10. A method for performing a biological reaction at two or more different temperatures, the method comprising the steps of: a) providing the thermal cycling system of claim 1 and placing a reaction vessel containing a biological mixture in the sleeve of the system:

b) positioning the sleeve in a position relative to the heat source that is set at a fixed temperature to allow the sleeve to achieve and maintain a first temperature of said biological reaction;

c) altering the relative position of the sleeve with respect to the heat source based on the temperature of the sleeve sensed by the temperature sensing means, so that the sleeve achieves and maintains a second different temperature of said biological reaction;

d) and thereby performing said biological reaction on the biological mixture at two or more different temperatures.

11. A method for performing a polymerase chain reaction amplification protocol comprising multiple cycles of three sequential temperature-dependent stages that constitute a single cycle of PCR: comprising template denaturation, primer annealing; and primer extension on a biological material, the method comprising the steps of:

a) providing the thermal cycling system of claim 2 and placing a reaction vessel containing a biological material and reagents for PCR in the sleeve of the system;

b) positioning the sleeve in a position relative to a heat source that is set at a fixed temperature to allow the sleeve to achieve and maintain a temperature for carrying out template denaturation;

c) altering the relative position of the sleeve with respect to the heat source based on the temperature of the sleeve sensed by the temperature-sensing means, so that the sleeve achieves and maintains a temperature for carrying out primer annealing;

d) altering the relative position of the sleeve with respect to the heat source based on the temperature of the sleeve sensed by the temperature-sensing means, so that the sleeve achieves and maintains a temperature for carrying out primer extension; and e) repeating the steps b), c) and d) to perform multiple cycles of PCR on the biological material.

12. The method of claim 10, which comprises maintaining said heat source fixed in place and moving said sleeve.

13. The method of claim 10, which comprises moving said heat source and maintaining said sleeve fixed in place.

14. The method of claim 10, wherein the sleeve is a metal sleeve with a temperature sensor.

15. The method of claim 14, including the step of altering the relative position of said sleeve with respect to said heat source to achieve and maintain said reaction vessel at a template denaturation temperature when said temperature sensor senses that the temperature of said sleeve approaches said template denaturation temperature.

16. The method of claim 15, including the step of altering the relative position of said sleeve with respect to said heat source to achieve and maintain the reaction vessel at a primer annealing temperature when said temperature sensor senses that the temperature of said sleeve approaches said primer annealing temperature.

17. The method of claim 16, including the step of altering the relative position of said sleeve with respect to said heat source to achieve and maintain the reaction vessel at a primer extension temperature when said temperature sensor senses that the temperature of said sleeve approaches said primer extension temperature.

18. The method of claim 16, which comprises the steps of providing a processor with an algorithm to predict the temperature being experienced by said reaction vessel, and altering the relative position of said sleeve with respect to said heat source to achieve and maintain the temperature of said reaction vessel at a primer annealing temperature when said algorithm predicts that the temperature of said reaction vessel approaches a primer annealing temperature.

19. The method of claim 17, which comprises the steps of providing a processor with an algorithm to predict the temperature being experienced by said reaction vessel, and altering the relative position of said sleeve with respect to said heat source to achieve and maintain the temperature of said reaction vessel at a primer extension temperature when said algorithm predicts that the temperature of said reaction vessel approaches a primer extension temperature.

20. The method of claim 14, which comprises the steps of empirically determining the positions of said sleeve relative to said heat source for each desired temperature, providing an empirical formula thereof and converting said empirical formula into an algorithm, and altering the relative position of said sleeve with respect to said heat source to achieve and maintain a desired temperature in said reaction vessel when said algorithm determines that the temperature of said reaction vessel approaches the desired temperature.

21. The method of claim 20, which comprises the steps of empirically determining the positions of said sleeve relative to said heat source for a desired template denaturation temperature, providing an empirical formula thereof and converting said empirical formula into an algorithm and changing the relative position of said sleeve with respect to said heat source to achieve and maintain the desired template denaturation temperature in said reaction vessel when said algorithm determines that the temperature of said reaction vessel approaches the desired template denaturation temperature.

22. The method of claim 20, which comprises the steps of empirically determining the positions of said sleeve relative to said heat source for a desired primer annealing temperature, providing an empirical formula thereof and converting said empirical formula into an algorithm, and changing the relative position of said sleeve with respect to said heat source to achieve and maintain a desired primer annealing temperature in said reaction vessel when said algorithm determines that the temperature of said reaction vessel approaches a desired primer annealing temperature.

23. The method of claim 20, which comprises the steps of empirically determining the positions of said sleeve relative to said heat source for a desired primer extension temperature, providing an empirical formula thereof and converting said empirical formula into an algorithm, and changing the relative position of said sleeve with respect to said heat source to achieve and maintain a desired primer extension temperature in said reaction vessel when said algorithm determines that the temperature of said reaction vessel approaches a desired primer extension temperature.

24. The method of claim 20, which comprises providing said sleeve with small openings that allow material inside the reaction vessel to be excited and imaged as part of a fluorescence detection apparatus.

25. The method of claim 20, which comprises minimizing evaporation into the top of said vessel by placing a plug-style cap reaction vessel into said reaction vessel and by positioning said sleeve to extend up the sides of the reaction vessel, so that said plug will be heated.

26. The thermal cycling system, of claim 2, wherein said heat source is a block of heat retentive material including means to heat said block to, and maintain said block at a fixed temperature.

27. The thermal cycling system of claim 26, wherein said sleeve is configured and arranged to be movable.

28. The thermal cycling system of claim 27, wherein said temperature-sensing means is operatively associated with a processor which is downloaded with an algorithm to predict the temperature being experienced by said reaction vessel, said algorithm being based on a program to achieve and maintain a desired temperature in the reaction vessel.

29. The thermal cycling system of claim 27, wherein the positions of said sleeve relative to said heat source for achieving and maintaining the first and second temperatures were determined empirically to provide an empirical formula, and wherein said temperature-sensing means is operatively associated with a processor which is downloaded with an algorithm defining said empirical formula.

30. The thermal cycling system of claim 26, wherein said block is configured and arranged to be movable.

31. The thermal cycling system of claim 2, wherein said sleeve is provided with openings that are capable of allowing material inside said reaction vessel to be excited and imaged as part of a fluorescence detection apparatus.

32. The thermal cycling system of claim 2, further comprising a reaction vessel, wherein said reaction vessel includes a plug-style cap which is situated within said reaction vessel and wherein said sleeve extends up the sides of said reaction vessel, so that said plug will be heated and will minimize evaporation into the top of the reaction vessel.

33. The thermal cycling system of claim 1, wherein the thermal cycling system comprises a single heat source.

34. The thermal cycling system of claim 2, wherein the thermal cycling system comprises a single heat source.

* * * * *